United States Patent
Sohn

(10) Patent No.: US 12,376,884 B2
(45) Date of Patent: Aug. 5, 2025

(54) SPACER AND METHOD OF MANUFACTURING THE SAME

(71) Applicant: Jung-wan Sohn, Seongnam-si (KR)

(72) Inventor: Jung-wan Sohn, Seongnam-si (KR)

(73) Assignee: Jung-wan Sohn, Seongnam-si (KR)

( * ) Notice: Subject to any disclaimer, the term of this patent is extended or adjusted under 35 U.S.C. 154(b) by 754 days.

(21) Appl. No.: 17/534,822

(22) Filed: Nov. 24, 2021

(65) Prior Publication Data
US 2023/0014048 A1    Jan. 19, 2023

(30) Foreign Application Priority Data

Jul. 17, 2021    (KR) ........................ 10-2021-0093847

(51) Int. Cl.
| | |
|---|---|
| *A61B 17/56* | (2006.01) |
| *A61L 27/52* | (2006.01) |
| *A61L 27/54* | (2006.01) |
| *A61L 27/56* | (2006.01) |

(52) U.S. Cl.
CPC ............ *A61B 17/562* (2013.01); *A61L 27/52* (2013.01); *A61L 27/54* (2013.01); *A61L 27/56* (2013.01)

(58) Field of Classification Search
CPC .... A61B 17/562; A61F 2/441; A61F 2/30756; A61F 2/30724; A61L 27/58
See application file for complete search history.

(56) References Cited

U.S. PATENT DOCUMENTS

| | | | |
|---|---|---|---|
| 7,648,713 B2 * | 1/2010 | Sawhney | A61L 31/145 424/9.4 |
| 9,314,339 B2 * | 4/2016 | Mansmann | A61L 27/56 |
| 9,770,337 B2 | 9/2017 | Shohat | |
| 11,612,754 B2 * | 3/2023 | Limem | A61N 1/375 424/426 |
| 2005/0278029 A1 * | 12/2005 | Trieu | A61F 2/441 623/23.74 |
| 2007/0118218 A1 * | 5/2007 | Hooper | A61B 17/562 623/14.12 |

(Continued)

FOREIGN PATENT DOCUMENTS

| | | | | |
|---|---|---|---|---|
| EP | 3409239 A1 * | 12/2018 | ............. | A61F 2/022 |
| KR | 100980170 B1 | 8/2010 | | |

(Continued)

*Primary Examiner* — Sarah W Aleman
(74) *Attorney, Agent, or Firm* — BROADVIEW IP LAW, PC

(57) ABSTRACT

The disclosure relates to a spacer using a hydrogel for treatment that aids in growth or bonding of living tissues after surgery or treatment of joints, muscles, or ligaments. The spacer includes a support sheet formed of a biodegradable hydrogel material having a water-soluble polymer network structure, and a pouch formed of a biodegradable material, as a sealing bag-shaped member surrounding the support sheet, and the support sheet is formed to dissolve in a body fluid faster than the pouch. Therefore, the spacer and a method of manufacturing the spacer according to the disclosure may eliminate cost and stress because there is no need for a subsequent removal operation, while stabilizing a surgical site and reducing pain, and particularly, adjust a drug delivery rate adaptively according to different recovery rates or tissue regeneration rates for different ages of patients.

2 Claims, 6 Drawing Sheets

(56) References Cited

U.S. PATENT DOCUMENTS

| | | | | |
|---|---|---|---|---|
| 2007/0184033 A1* | 8/2007 | Sevrain | ............... | A61P 19/00 |
| | | | | 424/423 |
| 2009/0105826 A1* | 4/2009 | McLeod | ............. | A61F 2/442 |
| | | | | 606/300 |
| 2009/0131939 A1* | 5/2009 | Ahrens | ............. | A61F 2/4405 |
| | | | | 623/17.11 |
| 2009/0234457 A1* | 9/2009 | Lotz | ................ | A61L 27/52 |
| | | | | 623/1.15 |
| 2010/0256766 A1* | 10/2010 | Hibri | ................ | A61F 2/4611 |
| | | | | 623/17.16 |
| 2018/0000603 A1 | 1/2018 | Shohat | | |
| 2018/0064544 A1* | 3/2018 | Grotz | ................ | A61L 27/54 |

FOREIGN PATENT DOCUMENTS

| | | | | |
|---|---|---|---|---|
| KR | 102206827 B1 | 1/2021 | | |
| WO | WO-2019025982 A1 * | 2/2019 | ........... | A61B 17/562 |

* cited by examiner

SPACER AND METHOD OF MANUFACTURING THE SAME

CROSS-REFERENCE TO RELATED APPLICATION(S)

This application is based on and claims priority under 35 U.S.C. § 119 to Korean Patent Application No. 10-2021-0093847, filed on Jul. 17, 2020, in the Korean Intellectual Property Office, the disclosure of which is incorporated by reference herein in its entirety.

BACKGROUND

1. Field

The disclosure relates to a spacer, and more particularly, to a spacer using a hydrogel for treatment that aids in growth or bonding of living tissues after surgery or treatment of joints, muscles, or ligaments.

2. Description of Related Art

Conventionally, even when a space is formed due to tissue damage or disconnection in a surgical site such as a muscle or a joint, surgery is usually completed by enclosing a ligament and tissues with a suture.

For example, in the case of rotator cuff repair illustrated in FIG. 1, a surgeon makes a partial incision and then inserts an arthroscopy through the incised part to perform an operation, while looking at a monitor screen, rather than directly observing the inside of a joint.

As a result, the distance between the distal end of a surgical instrument and the hand is long, and the surgical instrument should be indirectly controlled through a monitor. Unless the surgeon is highly skilled, one hour or more is taken for the operation after general anesthesia.

Moreover, to enable renewable tissues of the surgical site to recover and the suture condition to settle after the surgery, continuous rehabilitation within a fixed time is required.

However, when muscles are not recovered due to the empty space in the surgical site, rehabilitation movements cause considerable pain. Accordingly, the rehabilitation process is inevitably a series of tremendous pain.

To solve this problem, a technology has been developed to facilitate rehabilitation by inserting a tube-shaped instrument into a surgical site and filling the tube with liquid through a special nozzle during surgery to protect the surgical site and minimize movements of the surgical site during a rehabilitation process, as disclosed in U.S. Pat. No. 9,770,337-B2.

However, since leakage of the liquid filled in the tube should be prevented in the prior art, precision mechanisms having special structures should be installed at the end of the tube so that a nozzle insertion hole does not remain in the tube after the nozzle for liquid injection is removed from the tube.

In addition, because the tube should be prevented from melting inside the body to prevent liquid leakage, a separate removal operation is required to remove the tube later, which slows a patient's recovery and incurs a lot of cost.

In the prior art, although ligament tissues may be recovered by attaching a biodegradable polymer such as collagen to a ligament in a ligament restoration procedure, a biodegradable hydrogel support alone is weak in strength, it is difficult to fix collagen to a target body tissue, and collagen is easily disturbed in the body after the procedure.

Therefore, there is a need for a technology of eliminating cost and stress by obviating the need for a subsequent removal surgery, while maintaining the advantage of stabilizing the surgical site and reducing pain as offered by the prior art.

Particularly, the rate of drug delivery needs to be adjusted due to different recovery rates and tissue regeneration rates depending on the type of an affected area or the age of a patient. Nonetheless, a technology for a spacer having a means for controlling the rate of drug delivery, which delivers a biodegradable drug and regenerates tissues, is yet to be specified.

SUMMARY

Provided are a spacer which eliminates cost and stress by obviating the need for a subsequent removal surgery, while still having the conventional advantages of stabilization of a surgical site and pain reduction, and particularly which has a means for controlling a drug delivery rate adaptively according to a recovery rate and a tissue regeneration rate which are different for different types of affected areas or different ages of patients, and a method of manufacturing the spacer.

Additional aspects will be set forth in part in the description which follows and, in part, will be apparent from the description, or may be learned by practice of the presented embodiments of the disclosure.

According to an embodiment of the disclosure, a spacer includes a support sheet formed of a biodegradable hydrogel material having a water-soluble polymer network structure, and a pouch formed of a biodegradable material, as a sealing bag-shaped member surrounding the support sheet. The support sheet is formed to dissolve in a body fluid faster than the pouch.

The hydrogel material of the support sheet may contain a water-soluble drug.

Further, the pouch may be formed in a porous pore structure, and the body liquid in which the drug is dissolved may be discharged from the pouch to the outside through a plurality of micro-channels forming the pore structure.

A frame may be formed to extend along a predetermined part of the pouch, for maintaining a shape of the pouch against a pressure applied into a living tissue.

The frame may be a pore-dense band in which the pore structure is denser than a remaining structure of the pouch except for the frame, and the pore-dense band may include densely populated second micro-channels having a smaller diameter than the micro-channels.

According to an embodiment of the disclosure, a method of manufacturing a spacer includes manufacturing a hydrogel support sheet of a biodegradable polymer material, manufacturing a pouch of a biodegradable polymer material in the form of a bag, and inserting the support sheet into the pouch and sealing the pouch. There is no temporal precedence relationship between the manufacturing of the support sheet and the manufacturing of the pouch.

The method may further include injecting a drug into the support sheet before or after the sealing.

In this case, the manufacturing of the pouch may include manufacturing the pouch in a porous pore structure having a plurality of micro-channels formed therein.

Further, the manufacturing of the pouch may include adjusting the micro-channels to be large or small in size to allow the drug and a solution of the support sheet to flow out of the pouch at different rates, when the spacer is inserted into an affected area.

The manufacturing of the pouch may include forming micro-channels in the form of a band along a predetermined part of the pouch, smaller and denser than micro-channels in a remaining part except for the band, to make the band serve as a frame of the pouch.

The method may further include, after the sealing, drying the pouch having the support sheet embedded therein and then winding the pouch in the shape of a sheet roll.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Specific structures and functional descriptions in an embodiment of the disclosure are provided to describe an embodiment according to the inventive concept, and embodiments according to the inventive concept may be practiced in various manners. Further, the disclosure should not be interpreted as limited by the embodiments described herein, and it should be appreciated that the disclosure includes various changes, equivalents, or replacements within the spirit and scope of the disclosure.

The disclosure will be described below with reference to the attached drawings.

Figure 1:
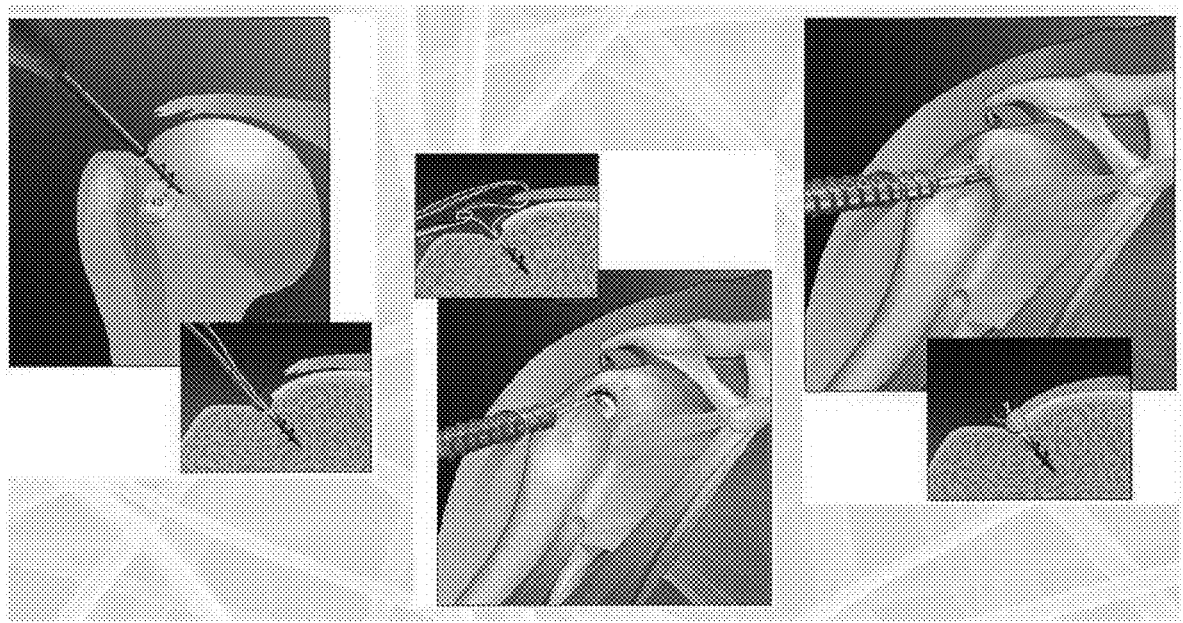
FIG. 1 is a diagram illustrating conventional rotator cuff repair.
Figure 2:
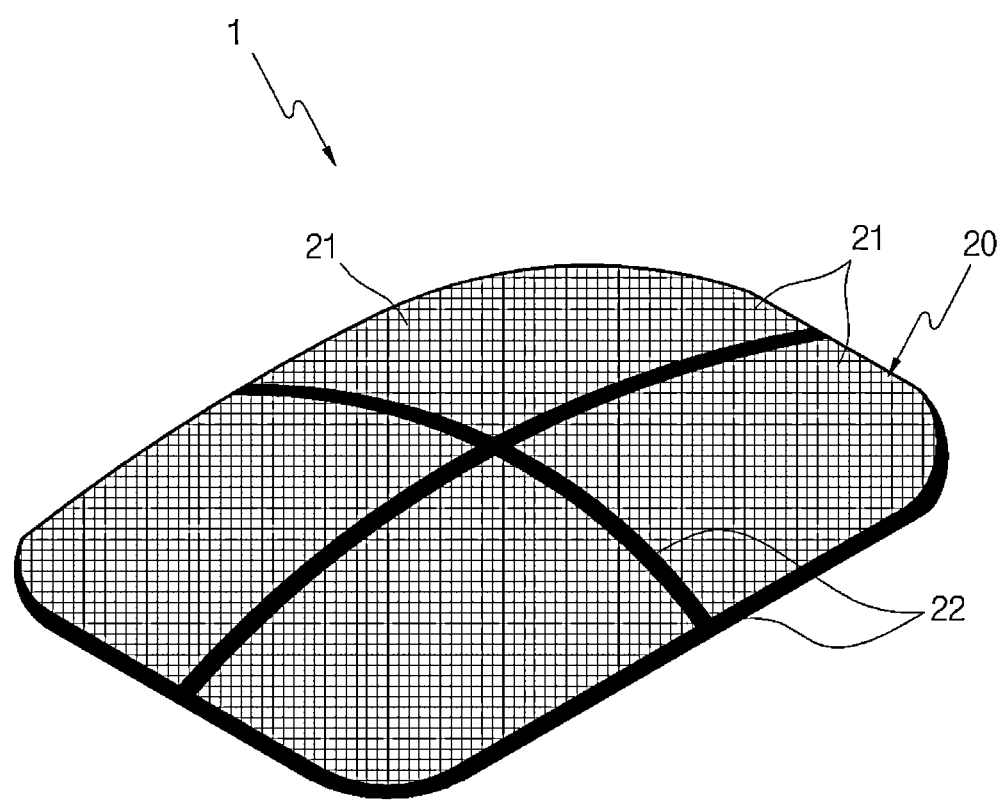
FIG. 2 is a perspective view illustrating a spacer according to the disclosure.
Figure 4:
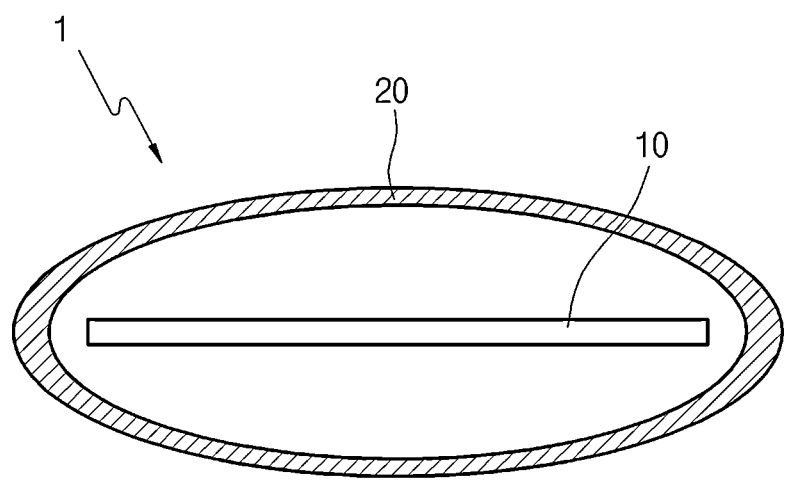
FIG. 4 is a side sectional view illustrating the spacer according to the disclosure.

A spacer 1 according to the disclosure includes a support sheet 10 and a pouch 20 for accommodating the support sheet 10 therein, as illustrated in FIGS. 2 and 4.

The support sheet 10 is formed of a biodegradable hydrogel having a water-soluble polymer network structure.

Hydrogels are three-dimensional network structures cross-linked by physical bonding (hydrogen bonding, van der Waals force, hydrophobic interaction, or polymer crystal) or chemical bonding (covalent bonding) of hydrophilic polymers. The hydrogels are insoluble in an aqueous environment and capable of retaining a significant amount of water.

Since hydrogels may be made from various water-soluble polymers, they have various chemical compositions and physical properties. In addition, as the hydrogels are easy to process, they may be transformed into various shapes depending on applications. As noted from successful applications in the peritoneum and various parts of the body, the hydrogels have high biocompatibility due to their high water content and physiochemical similarity to an extracellular matrix.

As such, a hydrogel may be widely used for tissue regeneration or bonding in an affected area by being inserted into a living body, while immersing a drug therein, owing to its biocompatibility and network structure.

In the conventional technology, however, the biodegradable hydrogel alone is weak, which makes it difficult to fix collagen or the like to the body tissue of the inserted site and easily disturbs the collagen after the procedure.

Therefore, to solve this problem, the spacer 1 according to the disclosure includes the pouch 20 which may control a dissolution rate, may maintain its shape while controlling a later-described drug discharge rate, and thus may be dissolved at a rate suitable for a treatment period of an affected area.

The pouch 20 is a member in the form of a sealing bag surrounding the support sheet 10 and formed of a biodegradable material. Particularly, the support sheet 10 is formed to dissolve in a body fluid faster than the pouch 20. Because the hydrogel material of which the support sheet 10 is formed may retain a water-soluble drug, when the pouch 20 dissolves at a rate similar to or greater than the dissolution rate of the support sheet 10, the support sheet 10 may be disturbed without continuously supplying the drug required for tissue regeneration to the affected area.

Figure 7:
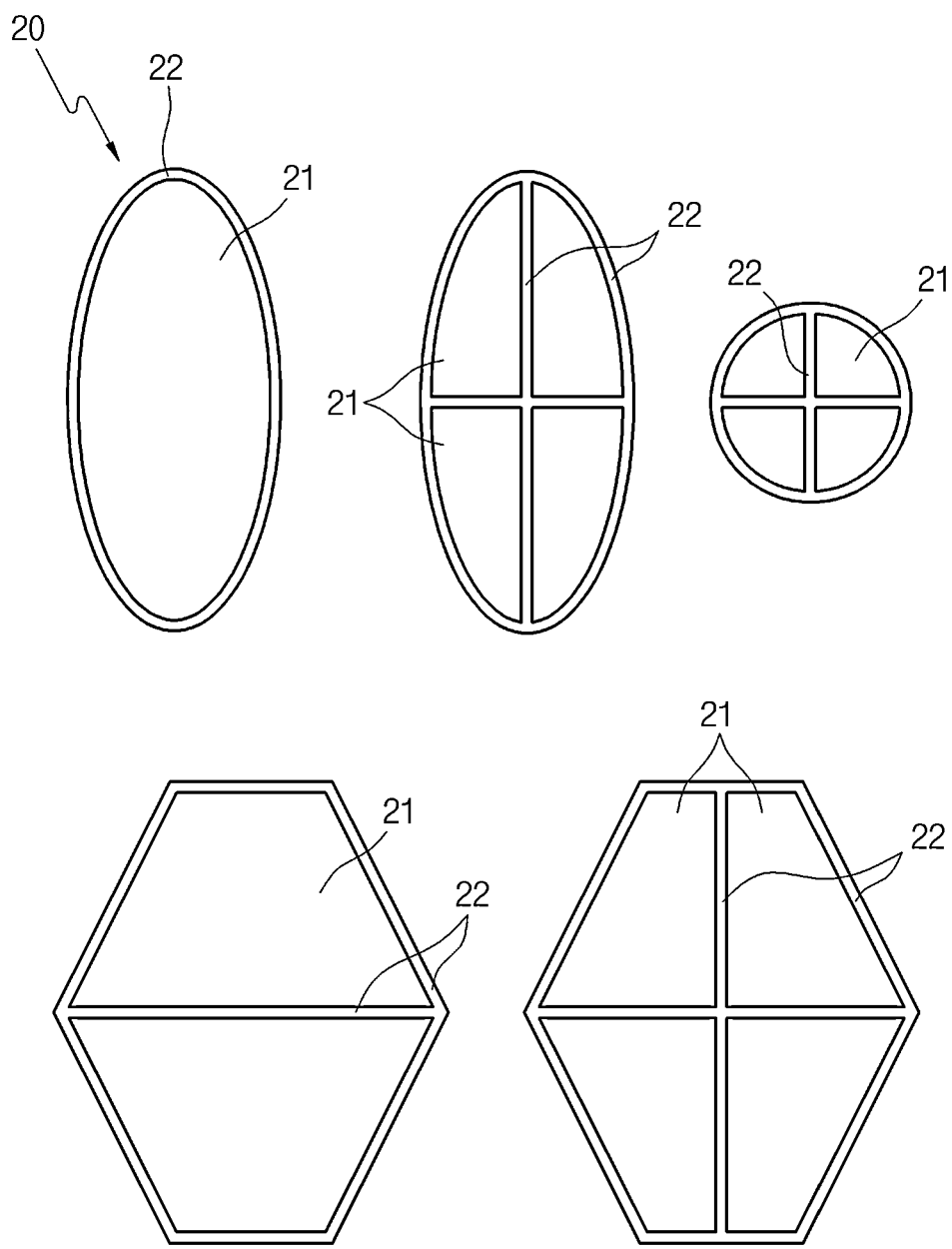
FIG. 7 is a plan view illustrating various modification examples of FIG. 3.

The pouch 20 may be formed in a porous pore structure, and a body fluid with a drug 30 dissolved therein may be discharged from the pouch 20 to the outside through a plurality of micro channels 21 forming the pore structure, as illustrated in FIG. 7.

The pouch 20 of the pore structure may be in the form of a mesh and have a different mesh size depending on the size of the mesh and a support part. The pouch 20 may also be formed in various sizes and shapes such as a rectangle and an oval.

In addition, biodegradable polymers such as collagen, CMC, chitosan, and hyaluronic acid may be used for the hydrogel of the support sheet 10, and the biodegradable polymers may be used alone or in combination.

Particularly, the sizes or densities of the micro-channels 21 may be adjusted in a manufacturing process of the pouch 20. Therefore, the size and density of the micro-channels 21 may be adjusted such that a necessary drug is continuously discharged from the pouch 20 for a period required for treatment or tissue regeneration according to the type of the affected area.

Even for the same type of affected area, the period required for tissue regeneration or treatment may vary considerably depending on age. Therefore, the pouch may be manufactured to be adjusted to a size suitable for a discharge rate so that the drug may be continuously discharged along micro-channels during the period, for each age group.

Figure 3:
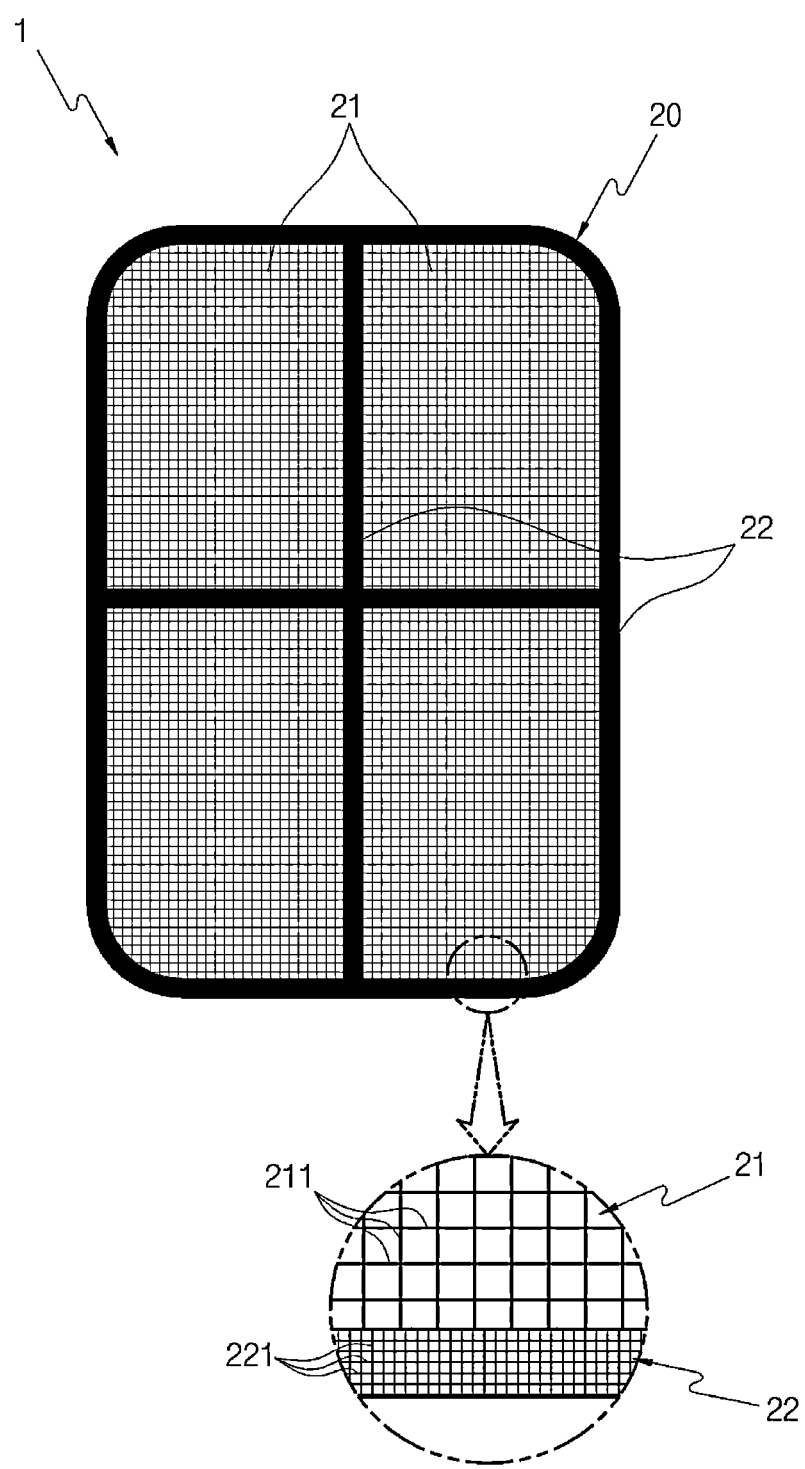
FIG. 3 is a plan view illustrating the spacer according to the disclosure.

In addition, as the pouch 20 is formed to include the frame 22 extending along a predetermined part as illustrated in FIGS. 2 and 3, the pouch 20 may maintain its shape even when pressure is applied inside the living tissue. Therefore, the spacer 1 may normally operate inside a substantially damaged tissue until the tissue is completely treated.

Particularly, the frame 22 is a pore-dense band in which the pore structure is denser than the remaining structure of the pouch 20 except for the frame 22, and the pore-dense band is formed such that second micro-channels having a smaller diameter than the micro-channels 21 are densely formed.

Therefore, as illustrated in the enlarged view of FIG. 3, frame cells 221 which are a representation of the second micro-channels on a plane are much smaller and denser than matrix cells 211 which are a representation of the micro-channels 21 on a plane.

Because the frame cells 221 are small in size and highly dense, partition walls defining the frame cells 221 are denser than the remaining part except for the frame 22, and the resulting increased density leads to a greater strength, thus enabling the frame 22 to operate as a frame.

Therefore, the spacer 1 according to the disclosure may fill an empty space which should be shaped before tissue regeneration of the affected part, and the frame 22 may be decomposed in the body after the internal support sheet 10 and the drug are completely discharged because the frame 22 is formed of a biodegradable material, which may obviate the need for a separate removal procedure.

A method of manufacturing the above-described spacer 1 according to the disclosure includes manufacturing the hydrogel support sheet 10 of a biodegradable polymer material, manufacturing the pouch 20 of a biodegradable polymer material in the form of a bag, and inserting the support sheet 10 into the pouch 20 and then sealing the pouch 20. There is no temporal relationship between the manufacturing of the support sheet 10 and the manufacturing of the pouch 20.

Figure 5:
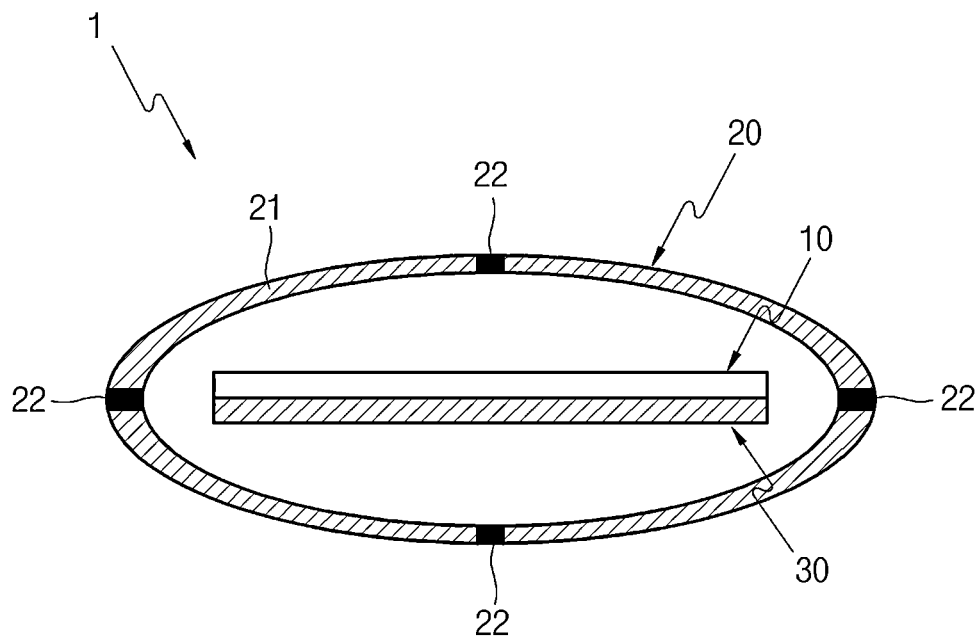
FIG. 5 is a side sectional view illustrating a modification example of FIG. 4.

The method may further include injecting the drug 30 into the support sheet 10 before or after the sealing. In this case, the drug 30 may be permeated into the hydrogel tissue forming the support sheet 10 in the manufacturing process of the support sheet 10, may be injected after the support sheet 10 is embedded and sealed inside the pouch 20, or may be made of a sheet-shaped solid and inserted into the pouch 20 together with the support sheet 10 as illustrated in FIG. 5.

During the manufacturing of the pouch 20, the pouch 20 may be manufactured in a porous structure having a plurality of micro-channels 21 formed therein.

Particularly during the manufacturing of the pouch 20, the size of the micro-channels 21 may be adjusted to be large or small, so that when the spacer 1 is inserted into the affected part, the drug and a solution of the support sheet flow out of the pouch at different rates. Therefore, the rate at which the drug is supplied from the pouch 20 is controlled according to the type of the affected area or the age of the patient as described before. Accordingly, even though a treatment period for tissue regeneration, for example, is different depending on the condition of the affected area or the patient, the drug may be continuously supplied to the affected area during a required period.

Further, during the manufacturing of the pouch 20, in the shape of a band elongated along a predetermined part of the pouch 20, micro-channels 21 are formed smaller and denser than micro-channels 21 in the remaining part except for the band. Therefore, the band may serve as a frame of the pouch 20.

The method may further include drying the pouch 20 with the support sheet 10 embedded therein and then winding the pouch 20 into a sheet roll, after the sealing.

Figure 6:
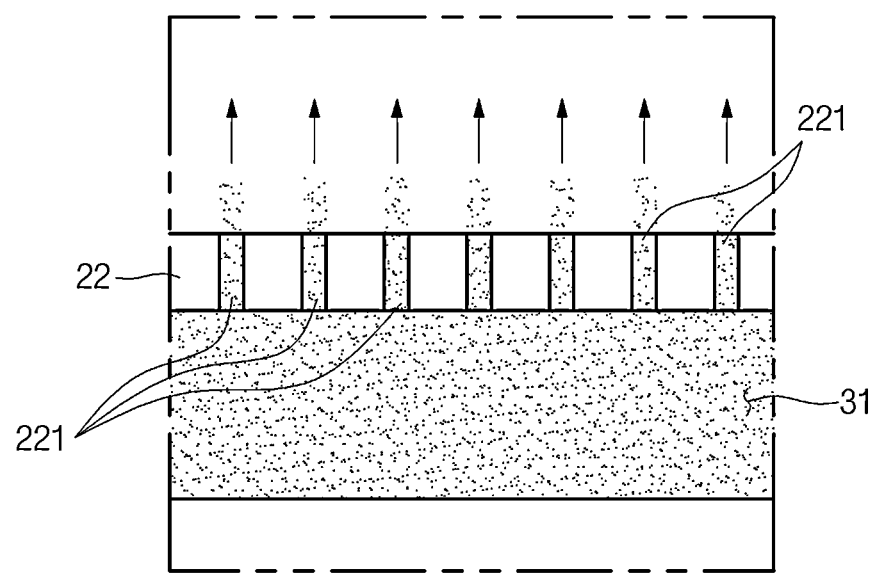
FIG. 6 is a partial enlarged view illustrating an action of the spacer according to the disclosure.

Particularly, the spacer wound in the form of a roll may be manufactured to a diameter that allows for endoscopic treatment. Therefore, the spacer may be injected into the affected area with an endoscopic instrument during the insertion of the spacer into the affected area. After the injection of the spacer into the affected area, the spacer may absorb a body fluid and swell to a size required for the affected area. Then, the spacer may supply the drug continuously to the affected area during the treatment period, as illustrated in FIG. 6.

Depending on the shape or type of the affected area, the pouch 20 may be manufactured in various shapes. FIG. 7 illustrates some exemplary pouches 20 of various shapes. However, the pouch may be manufactured in various shapes and sizes, not limited to the examples illustrated in FIG. 7.

As is apparent from the foregoing description, the spacer and the method of manufacturing the spacer according to the disclosure may eliminate cost and stress because there is no need for a subsequent removal operation, while stabilizing a surgical site and reducing pain as in the prior art. Particularly, a drug delivery rate may be adjusted adaptively according to different recovery rates or tissue regeneration rates for different ages of patients.

The disclosure described above is not limited by the above-described embodiments and the accompanying drawings, and it will be apparent to those skilled in the art that many replacement, modifications, and variations can be made without departing from the technical spirit and scope of the disclosure.

What is claimed is:

1. A spacer comprising:
    a support sheet formed of a biodegradable hydrogel material having a water-soluble polymer network structure; and
    a pouch formed of a biodegradable material, as a sealing bag-shaped member surrounding the support sheet,
    wherein the support sheet is formed to dissolve in a body fluid faster than the pouch, wherein the pouch is formed in a porous pore structure, and a plurality of first micro-channels forming the pore structure, wherein a frame is formed to extend along a predetermined part of the pouch, for maintaining a shape of the pouch against a pressure applied into a living tissue, wherein the frame is a pore-dense band in which the pore structure is denser than a remaining structure of the pouch except for the frame, and the pore-dense band includes densely populated second micro-channels having a smaller diameter than the plurality of first micro-channels.

2. The spacer according to claim 1, wherein the hydrogel material of the support sheet contains a water-soluble drug.

* * * * *